(12) United States Patent
West et al.

(10) Patent No.: US 6,346,094 B2
(45) Date of Patent: *Feb. 12, 2002

(54) PEN NEEDLE MAGAZINE

(75) Inventors: Robert E. West, Morristown; Tuan V. Nguyen, Rockaway; Michael A. Dibiasi, West Milford; Amir Ali Sharifi-Mehr, Millburn; Todd M. Chelak, Waldwick, all of NJ (US); Jeffrey R. McMurray, Bertrand, NE (US); Raymond Michael Layton; Donald D. Taubenheim, both of Holdrege, NE (US); Roger W. Hoeck, Loomis, NE (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/162,081

(22) Filed: Sep. 28, 1998

(51) Int. Cl.⁷ .................................................. A61M 5/31
(52) U.S. Cl. ...................................... 604/241; 206/365
(58) Field of Search ........................ 604/239, 240–243, 604/263, 192, 207–211; 206/366, 369, 370, 438

(56) References Cited

U.S. PATENT DOCUMENTS

| | | | | |
|---|---|---|---|---|
| 1,125,887 A | * | 1/1915 | Schimmel | |
| 1,881,415 A | * | 10/1932 | Tingleff | |
| 2,512,568 A | * | 6/1950 | Saffir | |
| D204,723 S | * | 5/1966 | Hamilton | |
| 3,382,865 A | * | 5/1968 | Worrall, Jr. | |
| 4,205,767 A | * | 6/1980 | Shackelford | 222/542 |
| 4,737,150 A | * | 4/1988 | Baeumle et al. | 604/239 |
| 5,224,596 A | * | 7/1993 | Kruger | 206/366 |
| 5,285,896 A | * | 2/1994 | Salatka et al. | 206/366 |
| 5,514,113 A | * | 5/1996 | Anderson et al. | 604/239 |
| 5,593,390 A | * | 1/1997 | Castellano et al. | 604/187 |
| 5,611,785 A | * | 3/1997 | Mito et al. | 604/239 |
| 5,775,498 A | * | 7/1999 | Kashanchi | 604/263 X |

* cited by examiner

Primary Examiner—Anhtuan T. Nguyen
(74) Attorney, Agent, or Firm—Alan W. Fiedler

(57) ABSTRACT

A pen needle magazine dispenser for holding and dispensing a novel pen needle assembly. The pen needle magazine dispenser includes a number of threaded sleeves within cavities that interact with threads on each pen needle assembly to attach the pen needle to a special adapter on a conventional medication delivery pen. The magazine dispenser includes a sterility barrier and a cap to cover the pen needles.

11 Claims, 8 Drawing Sheets

PEN NEEDLE MAGAZINE

BACKGROUND OF THE INVENTION

1. Field of the Invention

The subject invention relates to a pen needle magazine dispenser for a new pen needle and, more particularly, to a pen needle magazine that holds and dispenses sterile pen needles for medication delivery pens and that safely stores the needles after use.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula is mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication is drawn into the chamber of the syringe barrel by moving the plunger a selected distance in a proximal direction. The needle cannula is withdrawn from the vial, and the medication is injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. A prior art medication delivery pen is identified generally by the numeral 1 in FIG. 1. Pen 1 contains a cartridge with sufficient medication for several doses. The prior art cartridge has opposed proximal and distal ends. The distal end is closed by a pierceable and resealable rubber septum identified by the numeral 2 in FIG. 1. The proximal end receives a stopper in sliding fluid-tight engagement. The prior art cartridge is disposed in an elongate pen-like body 4 with a proximal end (not shown) and an opposed distal end 6. The proximal end of the pen body includes a plunger for selectively driving the stopper of the cartridge in the distal direction and a dose setting mechanism for determining the distance through which the plunger and stopper can move. Distal end 6 of pen body 4 includes an array of threads 8 for threaded engagement with a pen needle assembly 90. Pen needle assembly 90 includes a needle cannula 91 with opposed proximal and distal points 92 and 93 and a threaded mounting skirt 94 which surrounds the proximal tip 92. Mounting skirt 94 is threadably engageable with threads 8 on distal end 6 of pen body 4. A safety shield 95 is releasably engaged over distal point 93 and portions of mounting skirt 94 to prevent accidental needle sticks.

A person who must periodically inject doses of medication will carry a medication delivery pen 1 and a supply of pen needle assemblies 90. Each pen needle assembly 90 has its needle cannula 91 safely and sterility sealed in its own shield 95, and is accessed immediately prior to administering a dose of medication. Pen needle assembly 90 then is mounted to distal end 6 of prior art pen 1. This mounting causes proximal point 92 of needle cannula 91 to pierce rubber septum 2 of the cartridge, to place needle cannula 91 in communication with the medication in pen 1. Pen 1 then is used to inject the selected dose of medication. After completing the injection, needle assembly 90 is separated from pen 1 and is discarded. Pen 1 may be used repeatedly in this manner until the medication is exhausted. Such prior art pens offer many conveniences and efficiencies. However, the storage of unused needles and the final disposal of used needles has presented problems. In particular, supplies of new needles often are loosely scattered in the bottom of purses or briefcases, and used needles are often disposed of unsafely.

SUMMARY OF THE INVENTION

The subject invention relates to a storing and dispensing apparatus for needle assemblies used with hypodermic syringes and preferably a new type of pen needle that is designed to attach to an adapter having conventional threads that mate with threads 8 on medication delivery pens.

The pen needle dispenser of the present invention includes a magazine dispenser having a cover removably mounted on a container with a plurality of cavities, with each cavity dimensioned to receive a new type of pen needle assembly. The user inserts a special adapter on the medication delivery pen into one of the cavities and rotates the pen to mount an unused pen needle on the adapter on the medication delivery pen. After an injection has been performed, the used pen needle is returned to the cavity by inserting the used pen needle into the cavity and rotating the pen to detach the pen needle from the adapter on the pen.

An object of the present invention is to provide a user with a convenient way to carry, dispose of and keep track of their personal pen needle usage. The pen needle magazine dispenser is designed to be carried and contain a predetermined number of pen needles in respective cavities, with each cavity being sealed by a numbered label or sterility membrane. The numbered labels indicate how many unused pen needles remain in the pen needle magazine dispenser.

These and other aspects, features and advantages of the present invention will become apparent from the following detailed description taken in conjunction with the accompanying drawings.

DETAILED DESCRIPTION

Figure 1:
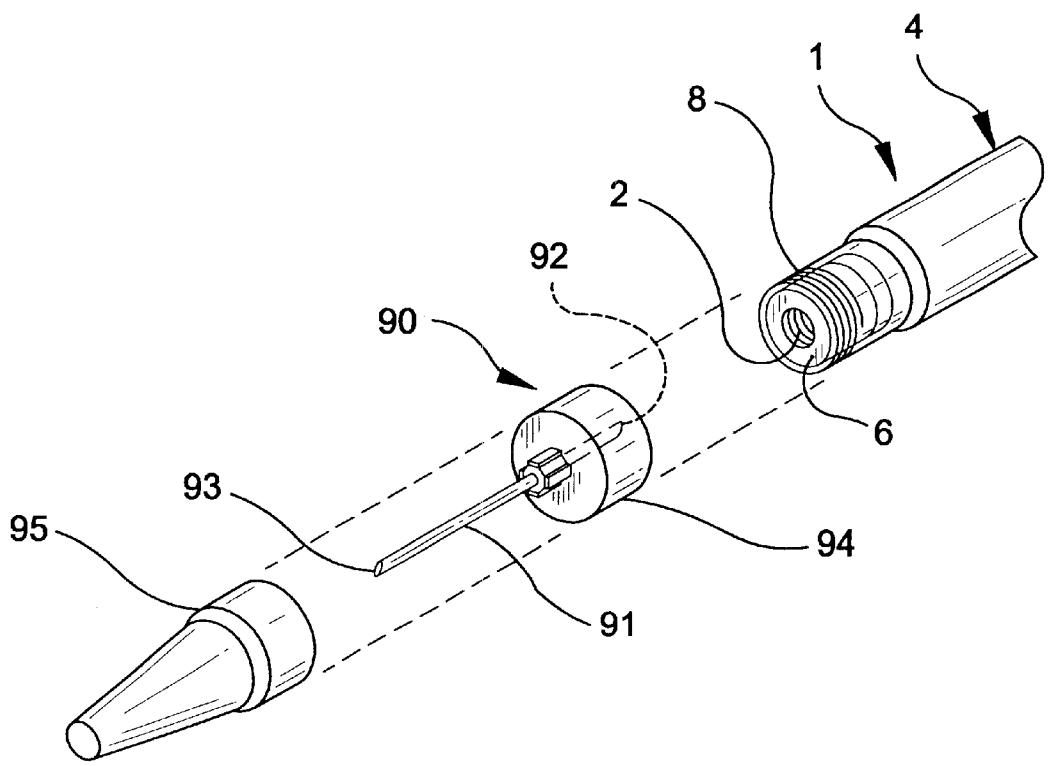
FIG. 1 is an exploded perspective view of a prior art pen needle and the distal end of a prior art medication delivery pen with which the present invention is intended to be used.
Figure 2:
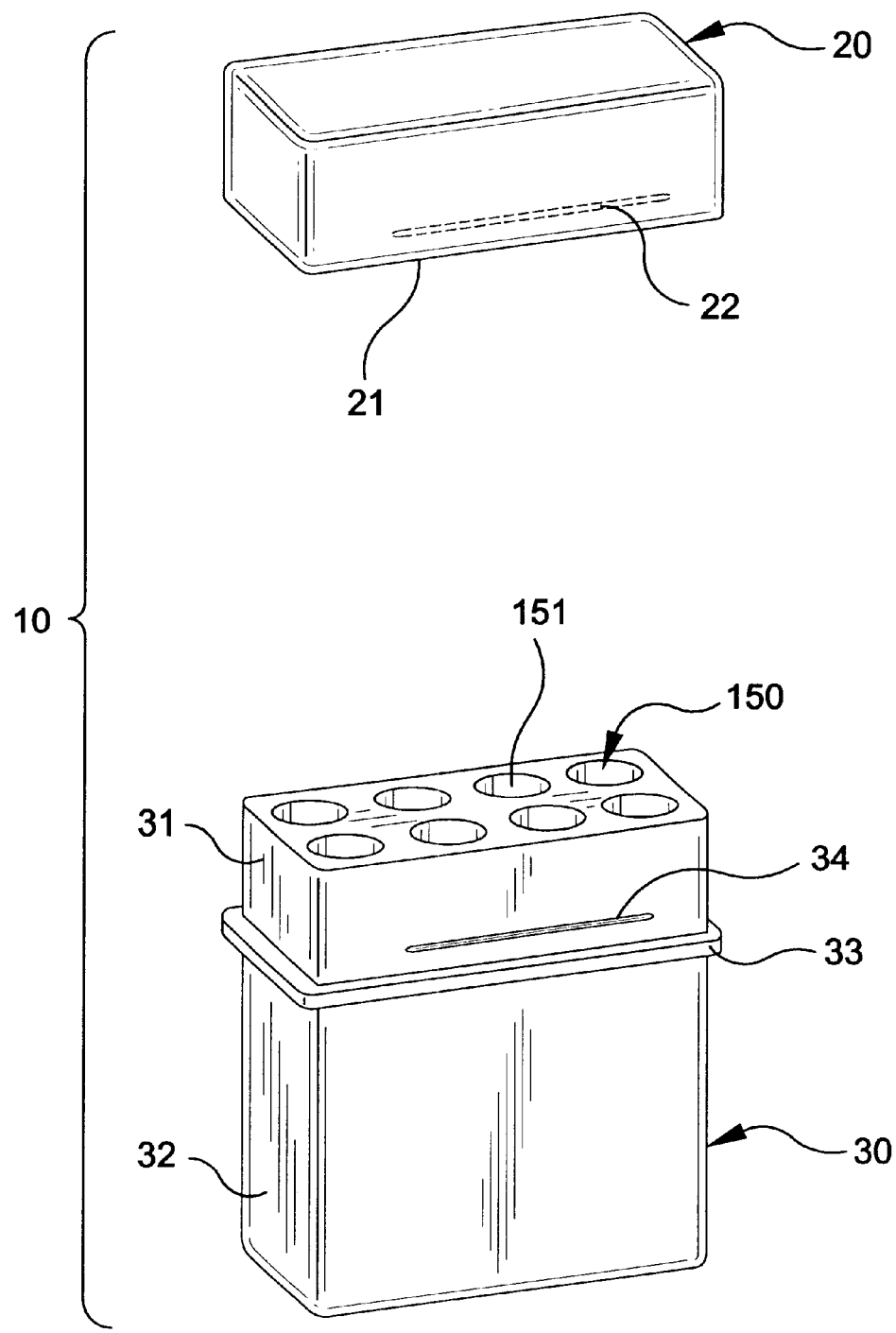
FIG. 2 is an exploded perspective view of a cover and a pen needle magazine dispenser according to the present invention.

FIG. 2 is an exploded perspective view of a pen needle magazine dispenser 10 according to the present invention. As shown in FIG. 2, pen needle magazine dispenser 10 includes a cover 20 and a container 30. Container 30 includes a top 31 and a bottom 32 with top 31 being covered by a sterility barrier 150. Container 30 also includes a flange 33 about its circumference that provides a stop for a bottom edge 21 of cover 20 and a detent 34 above flange 33 that interacts with a groove 22 within cover 20 to attach cover 20 on container 30. FIG. 2 also shows an indicia 151 on sterility barrier 150 corresponding to a location of a pen needle assembly 100.

Figure 3:
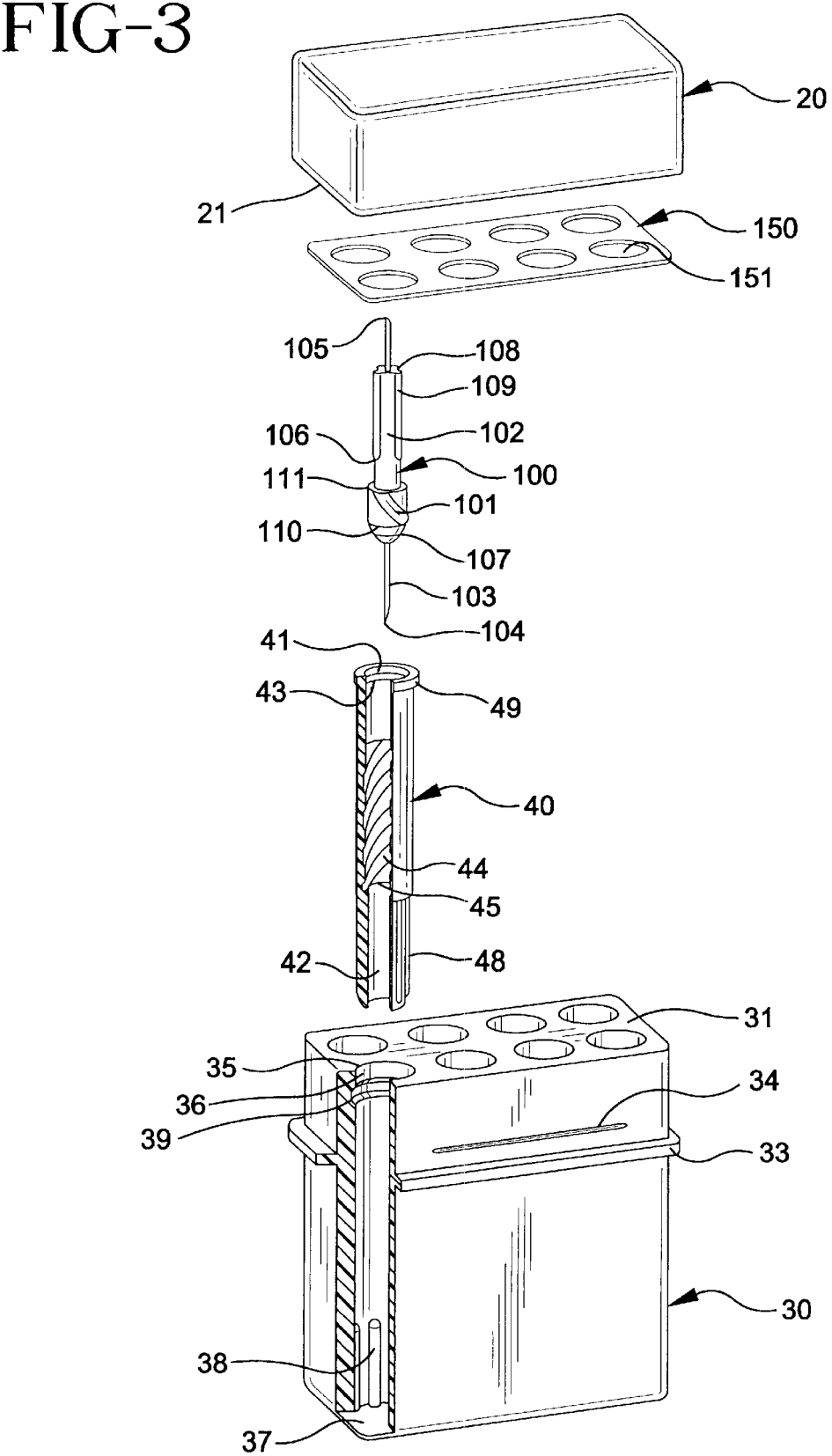
FIG. 3 is an exploded perspective view of the pen needle magazine dispenser shown in FIG. 2.

FIG. 3 is an exploded perspective view of pen needle magazine dispenser 10 shown in FIG. 2, and more clearly shows that container 30 includes a plurality of cavities 35, with each cavity 35 dimensioned to receive a sleeve 40 containing a pen needle assembly 100, described further below. Each pen needle assembly 100 is originally sealed in its respective sleeve 40 and cavity 35 by sterility barrier 150 that is attached to top 31 of container 30. Sterility barrier 150 provides sterility for unused pen needle assemblies 100 contained in each sleeve 40 and a simple means for the user to identify whether the pen needle assembly in a particular sleeve has been used.

Pen needle magazine dispenser 10 is initially loaded with a predetermined number of pen needle assemblies 100 in the sleeves in the plurality of cavities 35, with all of the cavities 35 being sealed by sterility barrier 150 and having an indicia 151 thereon corresponding to each pen needle assembly 100. Sterility barrier 150 is scored at the location of each sleeve 40 without, of course, affecting the integrity of the seal to allow for controlled breaking when adapter 50 on medication delivery pen 1 is pressed through label 150 when loading pen needle assembly 100 on adapter 50. The controlled breaking of the scored area allows adapter 50 on medication delivery pen 1 to be inserted through label 150 to mate with pen needle assembly 100 within sleeve 40.

As described above, container 30 includes a plurality of cavities 35 that are dimensioned to receive pen needle assemblies 100, as more clearly shown in FIGS. 3 and 4 and further described below. FIG. 3 shows a cross-sectional view of one of said plurality of cavities 35 and FIG. 4 more clearly shows adapter 50. As shown in FIG. 3, each cavity 35 includes an open end 36 and a closed end 37. Closed end 37 includes a plurality of anti-rotation ribs 38 that engage and are pressed fit together with a plurality of anti-rotation ribs 48 on the exterior of a sleeve 40, described below. Open end 36 includes a groove 39 that receives a flange 49 on sleeve 40 to hold sleeve 40 within cavity 35.

Sleeve 40 includes a first and second open end 41 and 42 with flange 49 surrounding open end 41. Open end 41 also includes a retention groove 43 for receiving a snap ring 55 on adapter 50, described below. Sleeve 40 also includes a set of threads 44 therein that end at a shoulder 45 near second open end 42 having a smaller diameter than open end 41. Second open end 42 is surrounded by a plurality of anti-rotation ribs 48 that mate with anti-rotation ribs 38 within cavity 35 to prevent rotation of sleeve 40 within cavity 35 and provide for both parts to be firmly pressed fit together. Of course, adhesives could also be added to prevent rotation and attach both parts together or other interacting shapes could be used within cavity 35 and in place of anti-rotation ribs 38 and 48, for example, open end 42 could have a multi-surfaced shape like a hexagon.

FIG. 3 also shows that pen needle assembly 100 includes a hub 102 having a plurality of keys 109 and a distal end 107 having a set of threads 101 thereon dimensioned to mate with the set of threads 44 within sleeve 40. A needle cannula 103 is mounted within hub 102 and includes a distal point 104 and a proximal point 105, wherein proximal point 105 extends from a proximal end 108 of hub 102 and distal point 104 extends out of distal end 107 on hub 102. Each key 109 extends from proximal end 108 toward distal end 107 and terminates at an edge 106.

Each pen needle assembly 100 is threaded into sleeve 40 by interaction of threads 101 on pen needle assembly 100 and threads 44 within sleeve 40 until distal end 107 of needle assembly 100 is received by shoulder 45 and held in place by second open end 42. This interaction prevents needle assembly 100 from accidentally separating from sleeve 40 until pen needle assembly 100 has been mounted on adapter 50. Pen needle assembly 100 also includes an edge 110 located between threads 101 and distal end 107 that bottoms out on shoulder 45 to stop movement of pen needle assembly 100 within sleeve 40. At the same time that flange 49 is received in groove 39 open end 42 makes contact with closed end 37 of cavity 35. The assembled pen needle assembly 100 and sleeve 40 are inserted into a cavity 35 within container 30 until flange 49 snaps into groove 39 within cavity 35 and anti-rotation ribs 48 and 38 are properly mated together. After a plurality of pen needle assemblies 100 have been loaded into pen needle magazine dispenser 10, sterility barrier 150 is attached to top 31 of container 30 using a heat seal or adhesive and cover 20 is snapped onto container 30.

Figure 4:
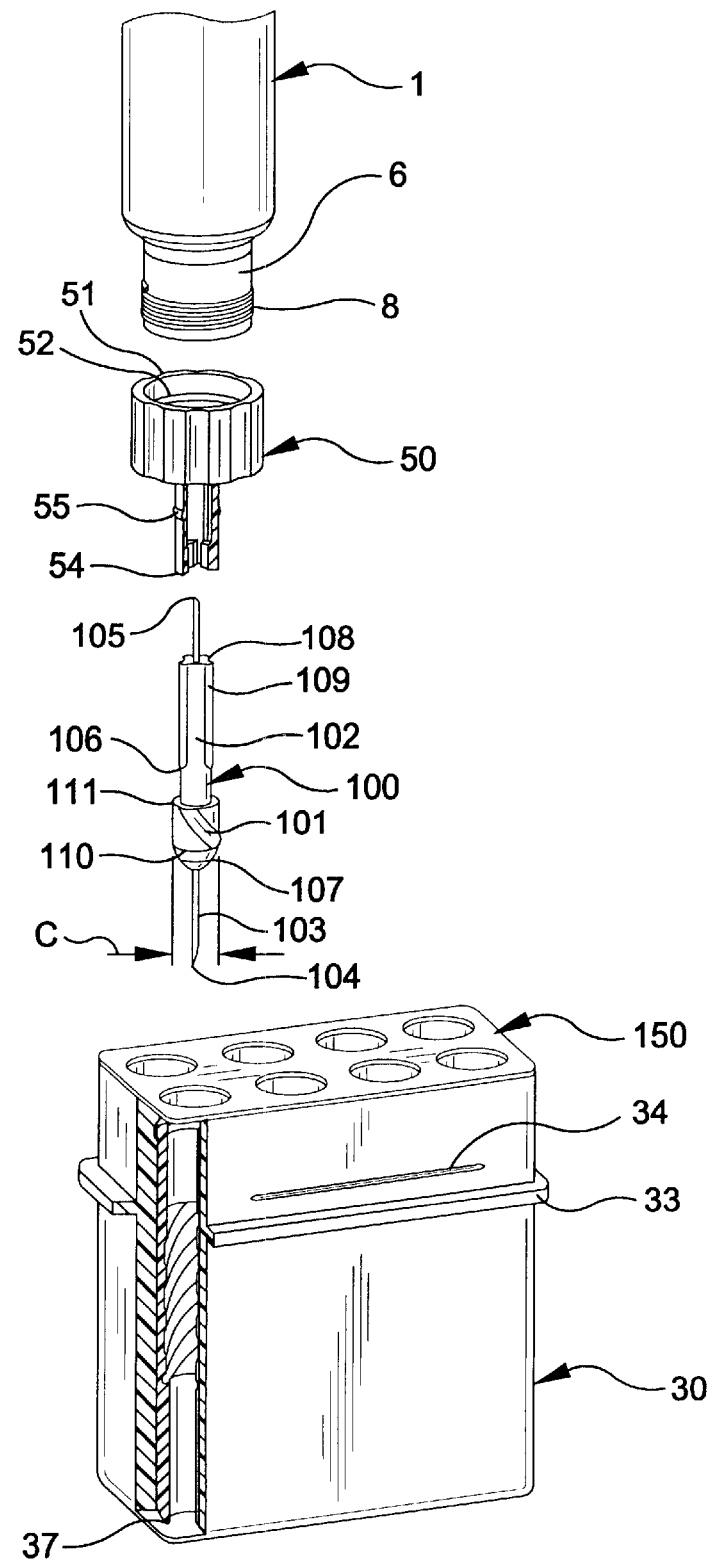
FIG. 4 is an exploded perspective view of a partially assembled pen needle magazine dispenser.

FIG. 4 is an exploded perspective view of a partially assembled pen needle magazine dispenser 10 having sleeve 40 mounted in cavity 35, showing pen needle assembly 100, an adapter 50 and a medication delivery pen 1 exploded therefrom. Adapter 50 includes an open proximal end 51 having a set of threads 52 dimensioned to mate with threads 8 on distal end 6 of conventional medication delivery pen 1. Adapter 50 also includes an opening 53 in its distal end 54. After adapter 50 has been threaded onto distal end 6 of pen 1, distal end 54 of adapter 50 is used to remove pen needle assembly 100 from sleeve 40 by inserting key 109 on proximal end 108 of needle assembly 100 into a key way 56 within adapter 50. When key 109 of needle assembly 100 is inserted into key way 56 in adapter 50, rotation of medication delivery pen 1 causes pen needle assembly 100 to rotate within sleeve 40 and move key 109 of needle assembly 100 along key way 56 into channel 57 in adapter 50. As key 109 moves from key way 56 into channel 57, edge 106 moves over a helical surface 58 so to lock key 109 in channel 57 and prevent pen needle assembly 100 from sliding out of adapter 50. Helical surface 58 in interaction with edge 106 also aids in driving pen needle assembly 100 into adapter 50 to a predetermined position where surface 111 is in contact with distal end 54 of adapter 50 to firmly hold pen needle assembly 100 within adapter 50.

Figure 5:
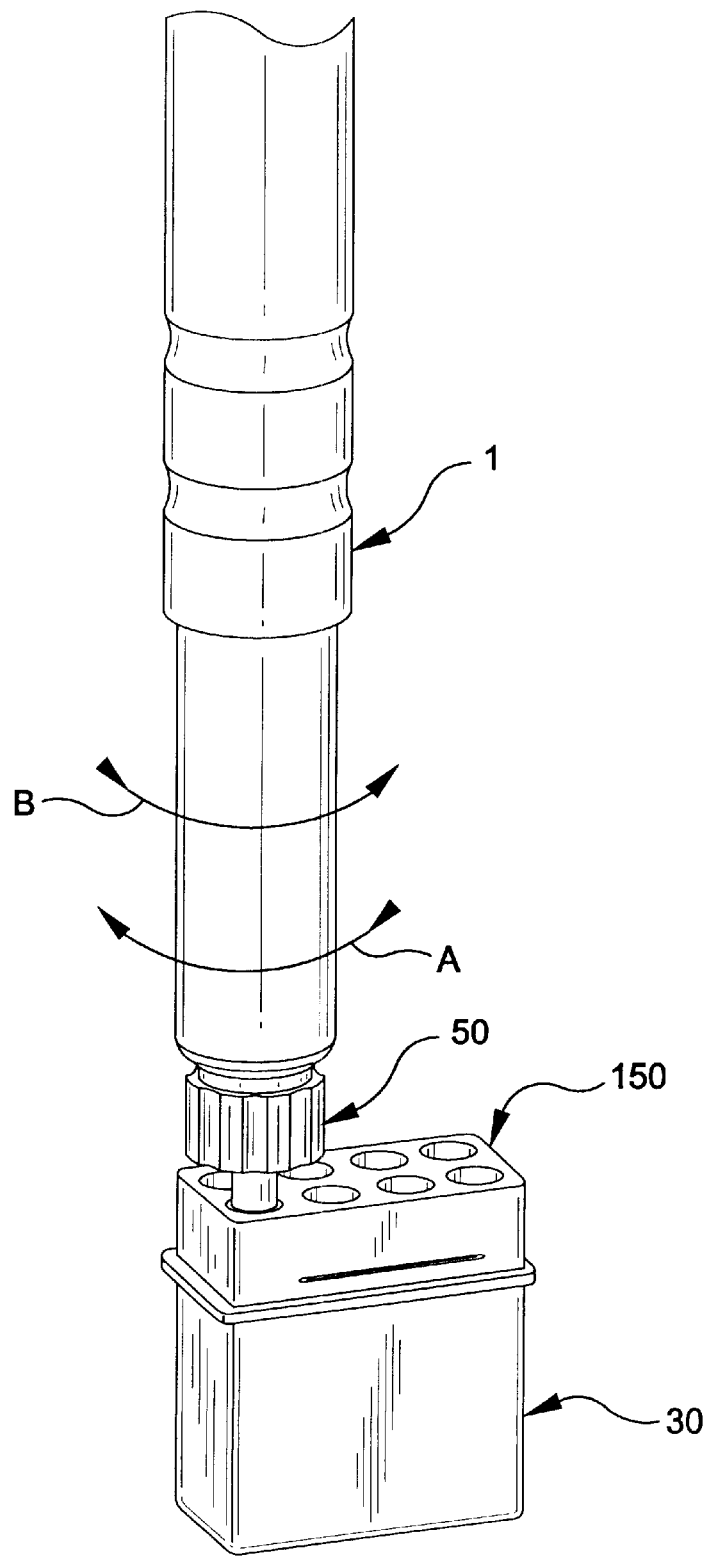
FIG. 5 is a perspective view of the mediation delivery pen and pen needle magazine dispenser, when attaching or removing the pen needle from the adapter.
Figure 6:
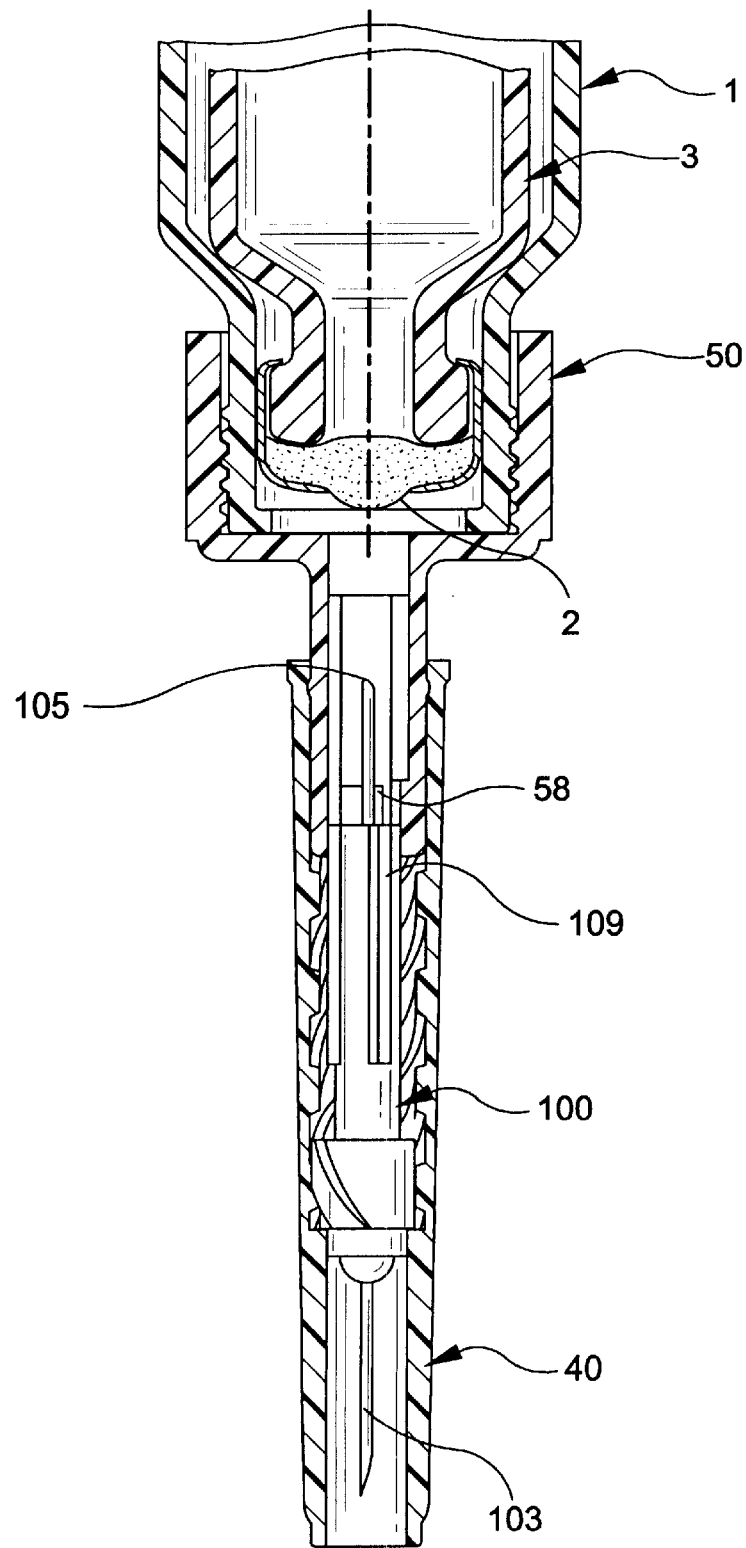
FIG. 6 is a cross-sectional view of a sleeve in the pen needle magazine dispenser prior to attaching the pen needle to the adapter.
Figure 7:
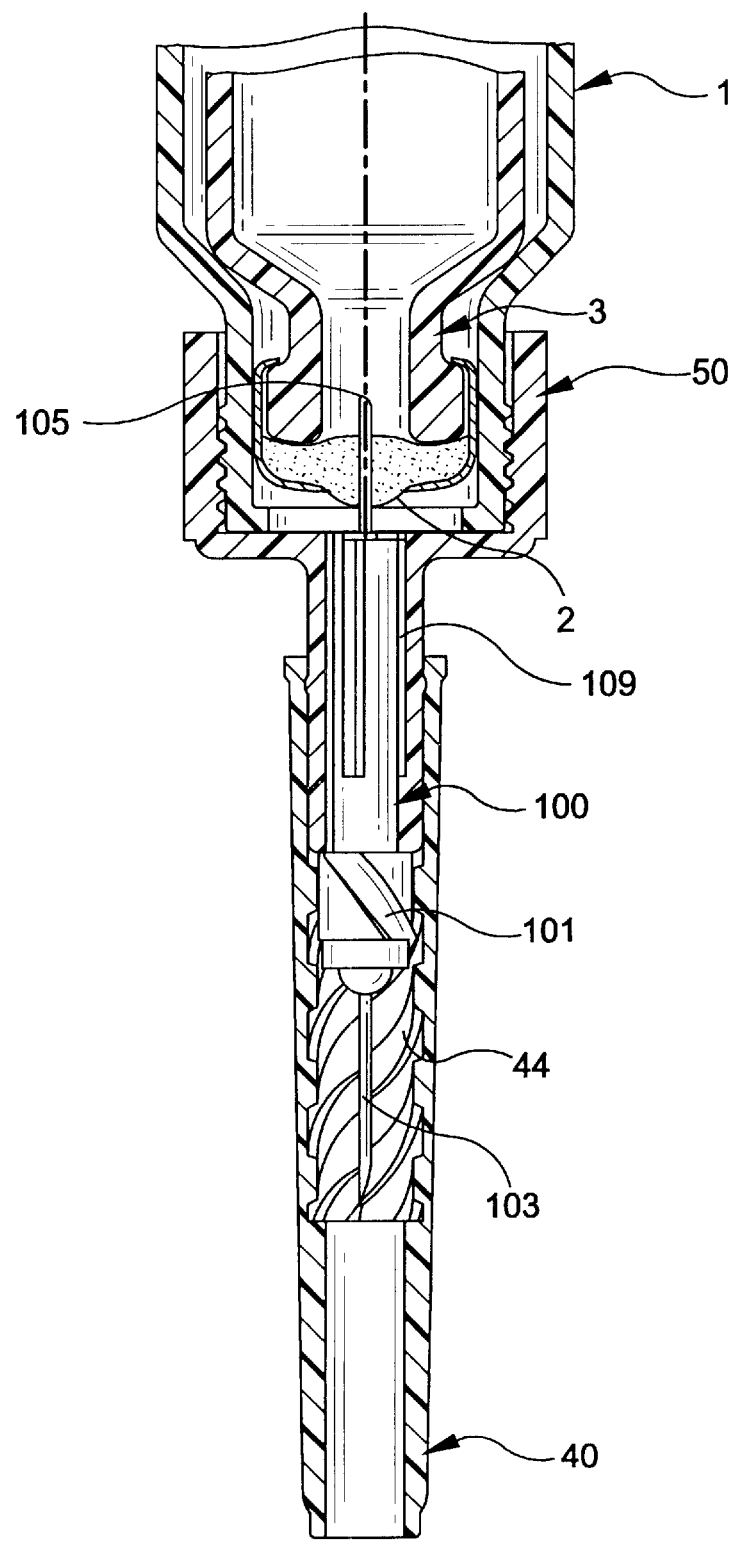
FIG. 7 is a cross-sectional view of the sleeve in the pen needle magazine dispenser after the pen needle has been attached to the adapter.
Figure 8:
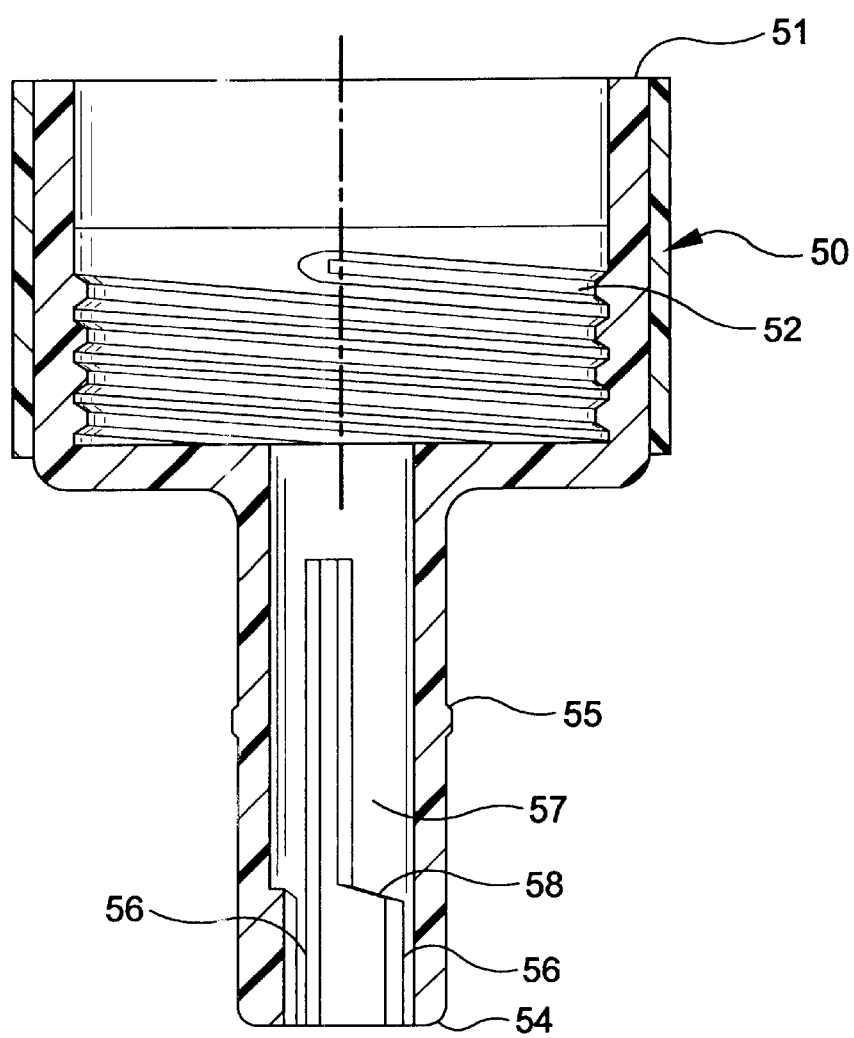
FIG. 8 is a cross-sectional view of the adapter.

As shown in FIGS. 6 and 7, as pen 1 is rotated in direction A, shown in FIG. 5, and needle assembly 100 is driven into adapter 50, proximal point 105 of pen needle assembly 100 pierces rubber septum 2 of a cartridge 3 in pen 1 to place needle cannula 103 in communication with medication contained within cartridge 3 in pen 1. Helical surface 58 and key 109 also holds proximal point 105 within rubber septum 2 and needle assembly 100 within adapter 50 during the injection of medication from cartridge 3 in pen 1. FIG. 6 is a cross-sectional view of sleeve 40 in pen needle magazine dispenser 10 prior to attaching pen needle assembly 100 onto adapter 50. FIG. 7 is a cross-sectional view of sleeve 40 after pen needle assembly 100 has been attached to adapter 50. FIG. 8 more clearly shows key way 56, channel 57 and helical surface 58 within adapter 50.

After use, the used pen needle assembly 100 mounted on adapter 50 on medication delivery pen 1 is reinserted into sleeve 40 until detent 55 and retention groove 43 mate and the set of threads 101 on pen needle assembly 100 come into contact with the set of threads 44 within sleeve 40. Medication delivery pen 1 is then rotated in the opposite direction B, shown in FIG. 5, to thread pen needle assembly 100 back into sleeve 40 and pen 1 is then pulled out of container 30 as pen needle assembly 100 is pulled out of adapter 50.

The use of sleeve 40 within container 30 not only provides an efficient mechanism to load a pen needle assembly 100 into container 30 but it also provides for ease of manufacturing, inspection of individual pen needle assemblies and improved quality control. In particular, if a damaged pen needle assembly 100 is found within sleeve 40, the entire sleeve 40 and pen needle assembly 100 can be disposed of and replaced with a new assembly 100 and sleeve 40 without loss of the remainder of container 30 and the other pen needle assemblies 100. It is also important to note that each sleeve 40 includes a flange 49 which provides for easy handling of sleeve 40 and pen needle assembly 100, when moving a loaded sleeve 40 to a cavity 35 within container 30 for insertion. By providing flange 49 on each sleeve 40, sleeve 40 can ride on conventional rails during the manufacturing operation. This is very important given the overall dimensions of the pen needle assembly 100. The present invention provides a needle assembly 100 that is significantly smaller that conventional pen needle assemblies 90. For example, needle assembly 100 of the present invention has been designed by the inventors so to have a reusable adapter 50 and an overall needle assembly diameter C, shown in FIG. 4, less than 0.150 inches, which is less than half the overall diameter of a conventional pen needle assembly 90. This design provides a needle assembly that can be carried by the user in a much smaller container and can be more easily packaged with similar needle assemblies in a common container. In addition, the reduction in overall size also reduces the material needed to fabricate the needle assembly and the volume of waste caused by the disposal of such needle assemblies.

While the invention has been described with respect to a preferred embodiment, it is apparent that various changes can be made without departing from the scope of the invention as defined by the appended claims. For example, adapter 50 can be integrally molded onto or permanently attached to distal end 6 of a medication delivery pen 1 rather than being a separate part.

What is claimed is:

1. A medication delivery pen and needle assembly comprising:
    a medication delivery pen; and
    a needle assembly including:
        a hub having a longitudinal axis;
        a key on said hub disposed substantially parallel to said longitudinal axis and not helical about said longitudinal axis for locking said hub to said medication delivery pen; and
        a cannula mounted within said hub and having a distal point and a proximal point.

2. An assembly according to claim 1, wherein said medication delivery pen includes a key way that receives said key on said needle assembly.

3. An assembly according to claim 2,
    wherein said medication delivery pen includes a channel that is connected to said key way by a helical surface, and
    wherein said key includes an edge that travels in said key way, over said helical surface and into said channel to lock said needle assembly in the medication delivery pen.

4. An assembly according to claim 2, wherein said proximal point of said cannula extends out of said hub such that when said key of said needle assembly is fully received within said key way in said medication delivery pen, said proximal point extends into said medication delivery pen a sufficient distance to pierce a septum within said medication delivery pen.

5. An assembly according to claim 1, wherein said key on said hub is received by a key way in a proximal end of an adapter mounted on said medication delivery pen, said adapter having a set of threads in its distal end that mate with a conventional set of threads on said medication delivery pen.

6. An assembly according to claim 5, wherein said hub includes means for moving said needle assembly into said adapter as said adapter and said needle assembly are rotated.

7. An assembly according to claim 6, wherein said means for moving said needle assembly into said adapter includes:
    a sleeve having a plurality of threads; and
    said needle assembly having a plurality of threads thereon that interact with said plurality of threads on said sleeve as said adapter and said needle assembly are rotated so to move said needle assembly into said adapter.

8. An assembly according to claim 7,
    wherein said sleeve includes a retention groove; and
    said adapter includes a detent that receives said retention groove to aid in attaching and unattaching said needle assembly from said adapter.

9. An assembly according to claim 6, wherein said means for moving said needle assembly into said adapter causes said key to move through said key way into a channel within said adapter.

10. An assembly according to claim 5,
    wherein said medication delivery pen includes a channel that is connected to said key way by a helical surface, and wherein said key includes an edge that travels in said key way, over said helical surface and into said channel to lock said needle assembly in said medication delivery pen.

11. A pen needle magazine for holding and dispensing a plurality of needle assemblies, said pen needle magazine comprising:
   a container having a plurality of cavities;
   a plurality of sleeves each mounted within one of said plurality of cavities and each of said plurality of sleeves having a set of threads; and
   a plurality of needle assemblies each having:
      a hub having a longitudinal axis;
      a set of threads on an outer surface thereof for mating with the threads within a respective cavity for inserting and removing the needle assembly from the sleeve; and
      a key substantially parallel to said longitudinal axis and not helical about said longitudinal axis for locking said needle assembly on a medication delivery pen.

* * * * *